United States Patent [19]

Siegfried et al.

[11] Patent Number: 4,946,669

[45] Date of Patent: Aug. 7, 1990

[54] HISTOLOGICAL FIXATIVES

[76] Inventors: Barry A. Siegfried, 12212 Foxpoint Dr., St. Louis, Mo. 63043; Eugene A. Holland, 204 E. Main, Washington, Mo. 63090

[21] Appl. No.: 107,026

[22] Filed: Oct. 9, 1987

[51] Int. Cl.$^5$ .......................... G01N 1/06; A01N 1/00
[52] U.S. Cl. .......................................... 424/4; 424/3; 424/75; 422/40
[58] Field of Search .................. 422/40; 424/3, 75, 4

[56] References Cited

U.S. PATENT DOCUMENTS

| | | | |
|---|---|---|---|
| 3,997,656 | 12/1976 | Wertlake et al. | 424/3 |
| 4,248,734 | 2/1981 | Romer-Sierra et al. | 428/22 |
| 4,278,715 | 7/1981 | Romer-Sierra et al. | 428/22 |
| 4,328,256 | 5/1982 | Romer-Sierra et al. | 422/40 |
| 4,404,181 | 9/1983 | Mauthner | 424/3 |
| 4,486,416 | 12/1984 | Soll et al. | 514/54 |
| 4,493,821 | 1/1985 | Harrison . | |
| 4,588,579 | 5/1986 | Bachhuber et al. . | |

*Primary Examiner*—Asok Pal
*Assistant Examiner*—James Saba
*Attorney, Agent, or Firm*—Robbins & Robbins

[57] ABSTRACT

A mercury and formaldehyde free histological fixative. The fixative employs standard non-toxic components comprising one or more alkanols, one or more diols and triols such as ethylene glycol, and one or more acids such as acetic and formic acid in an aqueous solution. A salt of a metal ion having an oxidation state of at least two may be added as an optional mordant. Osmotically active substances such as sodium chloride may be used as an option as desired to control osmotically induced cell volume changes.

21 Claims, No Drawings

HISTOLOGICAL FIXATIVES

BACKGROUND OF THE INVENTION

In the past, various formulations have been employed as histological fixatives to provide microscopic detail to sections of biological tissue. One such commonly used fixative is that known as B-5, which is an aqueous solution of mercuric chloride, sodium acetate and formaldehyde. Disadvantages of this fixative include dangerous exposure of laboratory personnel to toxic mercury and formaldehyde and the unpleasant odor of the latter, expense of disposing of the fixative in a safe manner because of its mercury content, excessive wear on microtome blades due to the hardening of the tissue by mercury and the necessity of removing elemental mercury from tissue sections by treatment with iodine. Due to precipitation of calomel and metallic mercury upon standing, fresh solutions must be prepared daily and any excess solutions create disposal problems.

The various disadvantages associated with the presence of mercury preclude the use of B-5 fixative as a routine fixative and allow its use only in situations where microscopic detail is of the greatest significance and importance, for example in the classification of a malignancy diagnosed as a malignant lymphoma. Fortunately, the handling of tissue following fixation by B-5 is almost the same as that of tissue fixed in a routine fixative, such as neutral buffered formalin, except for the use of iodine.

While various other fixatives for general use have been proposed that are mercury and formaldehyde free these have generally required the use of special non-standard chemicals and present staining problems of one type or another that do not lend them to widespread use.

SUMMARY OF THE INVENTION

By means of this invention there has been provided a histological fixative that is free of mercury and formaldehyde and is comprised of conventional components that are substantially non-toxic and relatively inexpensive. The term "histological fixative" as used herein is employed to include biological preservative for animal and plant tissue, preserving or fixing biological specimens such as frogs or the like for laboratory study and similar applications and other forms of preserving or fixing such tissue to include embalming. While for explanatory purposes the use is described in connection with preserving or fixing tissue for microscopic study it will be understood the employment is not limited thereto. The fixative is produced as a clear solution with a pleasant odor and extended shelf life. The tissue fixed by the fixative may be handled in the same manner as that treated by a routine fixative and yields microscopic detail greater than or equal to that produced by B-5 fixative containing mercury and formaldehyde.

Ventilation considered appropriate for the usual histology laboratory is adequate to keep exposure to the fixative within safe limits. The non-aqueous components of this fixative are present in sufficiently low concentration and the pH is sufficiently high (greater than 2) to allow safe disposal of small volumes of the fixative like those used under typical laboratory conditions (for example 500 ml. per day) in conventional sewage systems. A satisfactory microscopic appearance is obtained in sections of tissue immersed in the fixative for up to eight weeks, far longer than the few hours permitted by B-5 fixative.

The fixative of this invention constitutes a solution used as a histological fixative prior to application of hematoxylin and eosin stains, special histochemical stains or immunohistochemical stains. The fixative comprises a solvent of one or more alkanols such as methanol, one or more diols or triols such as ethylene glycol or glycerol, one or more acids such as formic acid and/or acetic acid and other carboxylic acids, picric acid, perchloric acid and the like, and water. The solute consists of mordants to enhance staining qualities and/or osmotically active agents to control osmotically induced cell volume changes and to preserve red blood cells. Examples of mordants and osmotically active agents are zinc chloride and sodium chloride respectively. Zinc chloride may also be employed for the dual function of mordant and osmotically active substance.

The fixative formulation is simply prepared from standard inexpensive laboratory chemicals and has a substantial shelf life. Handling and exposure represent no problems that are not encountered in a conventional laboratory. The fixative is employed for a variety of tissues and application of different stains with a wide range of tissues can be effected with enhanced specific staining and reduced non-specific staining.

DESCRIPTION OF THE INVENTION

The histological fixative of this invention is comprised of solvent components of one or more alkanols such as methanol or ethanol in a total concentration of about 200 to 800 milliliters per liter of solvent.

A further solvent component comprises one or more diols and triols in a total concentration of about 150 to about 700 milliliters per liter of solvent. Exemplary of such diols and triols are ethylene glycol, glycerol, propylene glycol and trimethylene glycol.

In addition, one or more acids such as formic acid and acetic acid are employed at a total concentration of about 0.01 to about 0.5 mole per liter of solvent. Water is added and constitutes the remainder of the solvent.

The solute consists of mordants, such as a salt with a metal ion having an oxidation state of two or more in a concentration of zero up to about 0.2 mole per liter of solvent. Zinc chloride is preferred but other salts, including those of strontium, calcium, barium and chromium, may also be employed. Also there may be employed picric acid and an alkali dichromate such as potassium dichromate.

In some instances of histological fixation of tissues, osmotically induced cell volume changes of the tissue may be encountered. In such cases, sodium chloride is included in the formulation as an osmotically active substance. In addition, sugars such as the polysaccharides, sucrose, glucose and the like may be employed for this purpose where desired.

Alkanol, diol and triol, acid and mordant components have been individually employed with other components in other formulations in preparing tissue for microscopy but have not been employed in applicant's novel formulation in the combination herein described. The individual components have met with acceptance for their individual characteristics. Thus the alkanols, particularly methanol and ethanol, are widely recognized as tissue fixatives. Generally, these alkanols are high concentrations in an aqueous solution such as 70% and 95% for ethanol. The diols and triols facilitate dehydration of the tissue and contribute to microscopic detail. Acetic acid is another acknowledged fixative and also counteracts the tissue shrinkage produced by the alkanols. Formic acid has been used primarily in decalcifying fixatives and has been found in this invention to provide satisfactory detail when used instead of acetic acid in the fixative. Water is necessary for optimal tissue preservation and increases the solubility of the zinc chloride or other salts in the fixative. Zinc chloride, or other appropriate salts as described above, is employed as a mordant.

As a typical example of the histological fixative of this invention there is listed below an exemplary formulation:

EXAMPLE

Ethanol, 400 mL/liter of fixative
Ethylene glycol, 300 mL/liter of fixative
Acetic acid, 10 mL/liter of fixative (0.17 mole per liter)
Zinc chloride, 5.8 g/liter of fixative
Water, remainder of fixative, i.e. about 290 mL/liter of fixative Various human tissues, including tonsil, vertebral bone marrow, and colon, were routinely immersed in the fixative for 1-8 hours, although immersion for up to 8 weeks gave a satisfactory microscopic appearance. Changes in tissue color and elasticity indicated rapid penetration, estimated as 2 mm/hour for tonsil. Gross tissue shrinkage was minimal. After fixation, bone marrow was decalcified with an ethylene diamine tetraacetic acid solution or formic acid. It was found that postfixation of soft tissues for 2 hours in neutral buffered formalin did not alter the microscopic appearance of tissue sections or staining characteristics. However, 2 hours of immersion in an aqueous phosphate buffer in lieu of postfixation gave poor results. Following fixation and optional postfixation, the tissue was dehydrated by a graded series of ethanol solutions. followed by xylene and then embedded in paraffin. Paraffin infiltrated the tissue thoroughly, producing tissue blocks with good cutting characteristics, including blocks containing large amounts of blood, fat, and dense smooth muscle such as uterine cervix.

Sections of tissue treated with this fixative had a satisfactory microscopic appearance using all of the following commonly used stains. In general, the tissue showed the good microscopic detail characteristic of B-5 fixative and the staining properties of a mordant-containing fixative such as Zenker's, an aqueous solution of mercuric chloride, potassium dichromate, acetic acid, and optionally sodium sulfate. Comments on the microscopic appearance are included as appropriate. It is generally observed that compared to formalin fixation, this fixative gives less non-specific staining, which tends to obscure or cloud the detecting stain.

STAINS

Giemsa—satisfactory appearance
Hematoxylin and eosin—nuclear detail comparable to B-5 fixed tissue
methyl green pyronin—less non-specific staining than formalin-fixed tissue
periodic acid Schiff—less non-specific staining than formalin-fixed tissue reticulin—little or no shrinkage was observed
Ulex europaeus agglutinin I (binds to fucose)--enhanced staining compared to formalin-fixed tissue
von Leder—less non-specific staining than formalin-fixed tissue The Leder stain for naphthol AS-D chloroacetate esterase, which cannot satisfactorily be performed on tissue fixed by B-5, gives good results using tissue fixed by the fixative described herein. The fixative also allows acceptable appearances of other histochemical stains as noted above, including periodic acid Schiff, methyl green pyronin and reticulin. Immunoperoxidase staining for fucose, using Ulex europaeus agglutinin I, is enhanced in tissue fixed by this fixative as compared to tissue fixed by neutral buffered formalin.

Sections of tissue treated with this fixative for up to 2 weeks also had a satisfactory microscopic appearance using the following immunohistochemical stains. Again, comments on the microscopic appearance are included as appropriate.

collagen, type IV—satisfactory appearance common leukocyte antigen—enhanced staining compared to formalin-fixed tissue
desmin—staining is comparable to that of ethanol-fixed tissue (stain cannot be performed on formalin-fixed tissue)
human epithelial keratin (AE1/AE3)--satisfactory appearance 1 S-100—no non-specific staining seen, unlike formalin fixed tissue
vimentin—less non-specific staining than formalin-fixed tissue As an example of the use of this fixative, following immersion of tissue in it for at least one hour, conventional processing may be carried out in a closed machine or otherwise. As an example, the tissue may be immersed in neutral buffered formalin, dehydrated by a series of aqueous ethanol solutions of gradually increasing concentration followed by xylene, infiltrated by molten paraffin, embedded in paraffin, and finally sectioned. The section is placed on a glass slide, stained with conventional stains as exemplified above, and examined microscopically. After examination, the slide may be preserved as in conventional practice.

Various changes and modifications may be made within this invention as will be apparent to those skilled in the art. Such changes and modifications are within the scope and teaching of this invention as defined in the claims appended hereto.

What is claimed is:

1. A mercury and formaldehyde free composition consisting essentially of an animal tissue histological fixative amount of a solution comprised of one or more alkanols as a tissue fixative, at least one member selected from the group consisting of an organic diol and triol having the capacity to dehydrate tissue and enhance microscopic detail, at least one acid to precipitate proteins, contribute to nuclear morphological detail, and increase penetration rate of fixative into tissue, 0 to about 700 millimoles per kilogram of solvent in the fixative of an osmotically active substance having the capacity to control osmotically induced cell volume changes, 0 to about 0.2 mole per liter of fixative of a mordant having the capacity to enhance staining characteristics, and water, the alkanols having a combined concentration of about 200 to about 800 milliliters per liter of fixative, the diols and triols having a combined concentration of about 150 to about 700 millileters per liter of fixative, and the acids having a combined concentration of about 0.01 to about 0.5 mole per liter of fixative.

2. The histological fixative of claim 1 in which an effective amount of the osmotically active substance is added and is at least one member selected from the group consisting of a salt, a monosaccharide, a disaccharide, and a water soluble polymer.

3. The histological fixative of claim 1 in which an effective amount of the mordant is added and is at least one member selected from the group consisting of a salt of a metal ion having an oxidation state of at least two, picric acid, and an alkali dichromate.

4. The histological fixture of claim 2 in which an effective amount of the mordant is added and is at least one member selected from the group consisting of a salt of a metal ion having an oxidating state of at least two, picric acid, and an alkali dichromate.

5. The histological fixative of claim 1 in which said alkanol is at least one member selected from the group consisting of methanol and ethanol; the diol and triol is at least one member selected from the group consisting of ethylene glycol, glycerol, propylene glycol and trimethylene glycol; and said acid is at least one member selected from the group consisting of formic acid, acetic acid and perchloric acid.

6. The histological fixative of claim 2 in which the osmotically active substance is at least one member selected from the group consisting of sodium chloride and zinc choloride, glucose, sucrose, dextran and polyvinylpyrrolidone.

7. The histological fixative of claim 3 in which the mordant is at least one member selected from the group consisting of zinc chloride, strontium chloride, calcium chloride, barium chloride and chromic chloride.

8. The histological fixative of claim 4 in which the osmotically active substance is at least one member selected from the group consisting of sodium chloride, zinc chloride, glucose, sucrose, dextran and polyvinylpyrrolidone, and the mordant is at least one member selected from the group consisting of zinc chloride, strontium chloride, calcium chloride, barium chloride and chromic chloride.

9. The histological fixative of claim 3 in which said alkonol is ethanol and has a concentration of about 400 milliliters per liter of fixative, said diol and triol is ethylene glycol and has a concentration of about 300 milliliters per liter of fixative, said acid is acetic acid and has a concentration of about 0.17 mole per liter of fixative, and said mordant is zinc chloride and has a concentration of about 5.8 grams per liter of fixative.

10. The histological fixative of claim 4 in which an effective amount of zinc chloride is employed as both the osmotically active substance and the mordant.

11. A method for preserving animal tissue which comprises treating said tissue with a mercury and formaldehyde free composition comprising an animal tissue histological fixative amount of a solution comprised of one or more alkanols as a tissue fixative, at least one member selected from the group consisting of an organic diol and triol as a dehydrating agent, at least one acid to precipitate proteins, contribute to nuclear morphological detail, and increase penetration rate of fixative into tissue, 0 to about 700 milliosmoles per kilogram of solvent in the fixative of an osmotically active substance having the capacity to control osmotically induced cell volume changes, 0 to about 0.2 mole per liter of fixative of a mordant having the capacity to enhance staining characteristics and water, the alkanols having a combined concentration of about 200 to about 800 milliliters per liter of fixative, the diols and triols having a combined concentration of about 150 to about 700 milliliters per combined of fixative, and the acids having a combined concentration of about 0.01 to about 0.5 mole per liter of fixative.

12. The method of claim 11 in which an effective amount of the osmotically active substance is added and is at least one member selected from the group consisting of a salt, a monosaccharide, a disaccharide, and a water soluble polymer.

13. The method of claim 18 in which an effective amount of the mordant is added and is at least one member selected from the group consisting of a salt of a metal ion having an oxidation state of at least two, picric acid, and an alkali dichromate.

14. The method of claim 12 in which an effective amount of the mordant is added and is at least one member selected from the group consisting of a salt of a metal ion having an oxidation state of at least two, picric acid, and an alkali dichromate.

15. The method of claim 11 in which the alkanol is at least one member selected from the group consisting of methanol and ethanol; the diol and triol is at least one member selected from the group consisting of ethylene glycol, glycerol, propylene glycol and trimethylene glycol; and said acid is at least one member selected from the group consisting of formic acid, acetic acid and perchloric acid.

16. The method of claim 12 in which the salt is at least one member selected from the group consisting of sodium chloride and zinc chloride; the monosaccharide is glucose; the disaccharide is sucrose; and the polymer is at least one member selected from the group consisting of dextran and polyvinylpyrrolidone.

17. The method of claim 13 in which the salt is at least one member selected from the group consisting of zinc chloride, strontium chloride, calcium chloride, barium chloride and chromic chloride.

18. The method of claim 14, in which the salt is at least one member selected from the group consisting of zinc chloride, strontium chloride, calcium chloride, barium chloride and chromic chloride.

19. The method of claim 11 in which said alkanol is ethanol and has a concentration of about 400 milliliters per liter of fixative, said diol and triol is ethylene glycol and has a concentration of about 300 milliliters per liters of fixative, said acid is acetic acid and has a concentration of about 0.17 mole per liter of fixative and said mordant is zinc chloride and has a concentration of about 5.8 grams per liter of fixative.

20. The method of claim 14 in which an effective amount of zinc chloride is employed as both the osmotically active substance and the mordant.

21. The method of claim 11 in which the animal tissue is prepared for microscopic examination by cutting a section of the animal tissue of suitable size for said examination and the aforesaid treating is effected upon said section of animal tissue.

* * * * *

UNITED STATES PATENT AND TRADEMARK OFFICE
CERTIFICATE OF CORRECTION

PATENT NO. : 4,946,669
DATED : August 7, 1990
INVENTOR(S) : Barry A. Siegfried and Eugene A. Holland It is certified that error appears in the above-identified patent and that said Letters Patent is hereby corrected as shown below:

In the Title, it should read -- LOW TOXICITY HISTOLOGICAL FIXATIVE WITHOUT MERCURY OR ALDEHYDES --. Column 3, line 63, the text beginning with the word "reticulin" should begin on a new line. Column 5, claim 4, line 12, the word "oxidating" should read -- oxidation --; claim 6, line 25, the word "choloride" should read -- chloride --; claim 9, line 40, the word "alkonol" should read -- alkanol --. Column 6, claim 11, line 6, the word "combined" should read -- liter --; claim 13, line 14, claim reference numeral "18" should read -- 11 --; claim 19, line 49, the word "liters" should read -- liter --.

Signed and Sealed this

Twenty-seventh Day of August, 1991

Attest:

HARRY F. MANBECK, JR.

Attesting Officer

Commissioner of Patents and Trademarks